(12) United States Patent  (10) Patent No.: US 9,155,651 B2
Ochoa  (45) Date of Patent: Oct. 13, 2015

(54) BACK SUPPORT SYSTEM

(71) Applicant: Leonardo Ochoa, Beaverton, OR (US)

(72) Inventor: Leonardo Ochoa, Beaverton, OR (US)

(73) Assignee: Leonardo Ochoa, Seattle, WA (US)

( * ) Notice: Subject to any disclaimer, the term of this patent is extended or adjusted under 35 U.S.C. 154(b) by 297 days.

(21) Appl. No.: 13/654,011

(22) Filed: Oct. 17, 2012

(65) Prior Publication Data

US 2013/0281901 A1  Oct. 24, 2013

Related U.S. Application Data

(60) Provisional application No. 61/548,605, filed on Oct. 18, 2011.

(51) Int. Cl.
*A61F 5/00* (2006.01)
*A61F 5/02* (2006.01)

(52) U.S. Cl.
CPC ..................... *A61F 5/028* (2013.01)

(58) Field of Classification Search
CPC ....... A61F 5/0585; A61F 5/028; A61F 5/055; A61F 5/24; A61F 5/0093; A61F 5/02; A61F 5/026; A41F 511/16; A41F 9/002; A61G 13/12; A41D 13/1245
USPC ........ 602/5, 17–19, 4, 20; 2/311–315, 44, 45, 2/22; 128/96.1, 98.1, 99.1, 100.1, 101.1, 128/845, 869
See application file for complete search history.

(56) References Cited

U.S. PATENT DOCUMENTS

| 26,628 | A | * | 12/1859 | Taylor | 602/19 |
|---|---|---|---|---|---|
| 199,463 | A | * | 1/1878 | Partridge | 602/19 |
| 221,568 | A | * | 11/1879 | Johnson | 602/19 |
| 443,764 | A | * | 12/1890 | Hilliard | 602/19 |
| 496,816 | A | * | 5/1893 | Corker | 602/19 |
| 664,250 | A | * | 12/1900 | Fitzpatrick | 602/19 |
| 714,124 | A | * | 11/1902 | Adams | 602/19 |
| 796,623 | A | * | 8/1905 | Bailey | 2/45 |
| 1,301,276 | A | * | 4/1919 | Kroetz | 602/19 |
| 1,812,529 | A | * | 6/1931 | Haulbrook et al. | 2/44 |
| 2,871,850 | A | * | 2/1959 | Peckham | 602/19 |
| 3,452,748 | A | * | 7/1969 | Caprio | 602/19 |
| 4,080,962 | A | * | 3/1978 | Berkeley | 602/19 |
| 4,949,888 | A | * | 8/1990 | May | 224/602 |
| 5,007,412 | A | * | 4/1991 | DeWall | 602/19 |
| 5,537,690 | A | * | 7/1996 | Johnson | 2/44 |
| 5,765,224 | A | * | 6/1998 | Johnson | 2/44 |
| 8,328,742 | B2 | * | 12/2012 | Bledsoe | 602/19 |
| 8,795,214 | B1 | * | 8/2014 | Conti | 602/19 |
| 2012/0022420 | A1 | * | 1/2012 | Sandifer et al. | 602/19 |

* cited by examiner

Primary Examiner — Kim M Lewis
(74) Attorney, Agent, or Firm — Bradley A. Forrest (57) ABSTRACT

A back support device including a flexible support adapted to be positioned adjacent a spine of a wearer, the flexible support extending along the spine in an "S" shape. A brace portion is coupled to the flexible support at ends of the flexible support, and is adapted to force the spring portion toward the spine as a wearer bends.

20 Claims, 6 Drawing Sheets

BACK SUPPORT SYSTEM

RELATED APPLICATION

This application claims priority to U.S. Provisional Application Ser. No. 61/548,605 (entitled Back Support System), filed Oct. 18, 2011) which is incorporated herein by reference.

BACKGROUND

Emergency medical technicians (EMTs) face a related common challenge in their daily duties. The heavy lifting of medical equipment and patients up and down flights of stairs places all EMTs at risk for experiencing frequent back injuries. Current back braces are designed to lock the back muscles and spine in one position, limiting mobility, creating discomfort, and restraining the user from doing their work.

SUMMARY

A back support device including a flexible support adapted to be positioned adjacent a spine of a wearer, the flexible support extending along the spine in an "S" bend shape. A brace portion is coupled to the flexible support at ends of the flexible support, and is adapted to force the flexible support toward the spine as a wearer bends.

In one embodiment, a method includes placing a flexible support adjacent a spine of a wearer, the flexible support extending along the spine in an "S" shape, and coupling a brace portion to the flexible support at ends of the flexible support, wherein the brace portion is positioned to force the flexible support toward the spine as a wearer bends. This method adds needed support to the bottom end of the flexible support to utilize the waistline as a fulcrum point.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Figure 1:
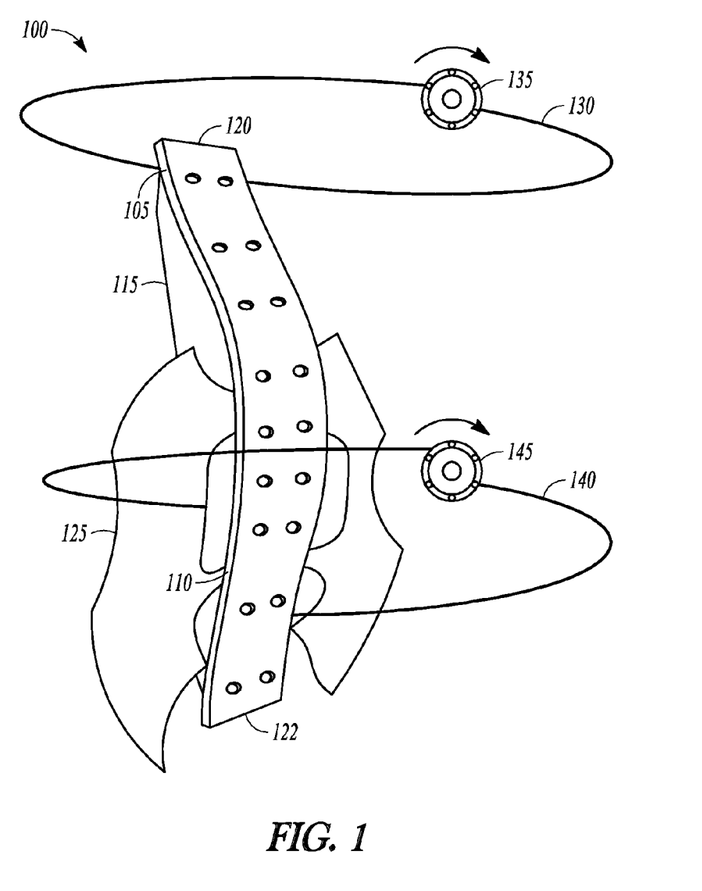
FIG. 1 is a perspective front view of an artificial spine system having an "S" shaped flexible support according to an example embodiment.
Figure 2:
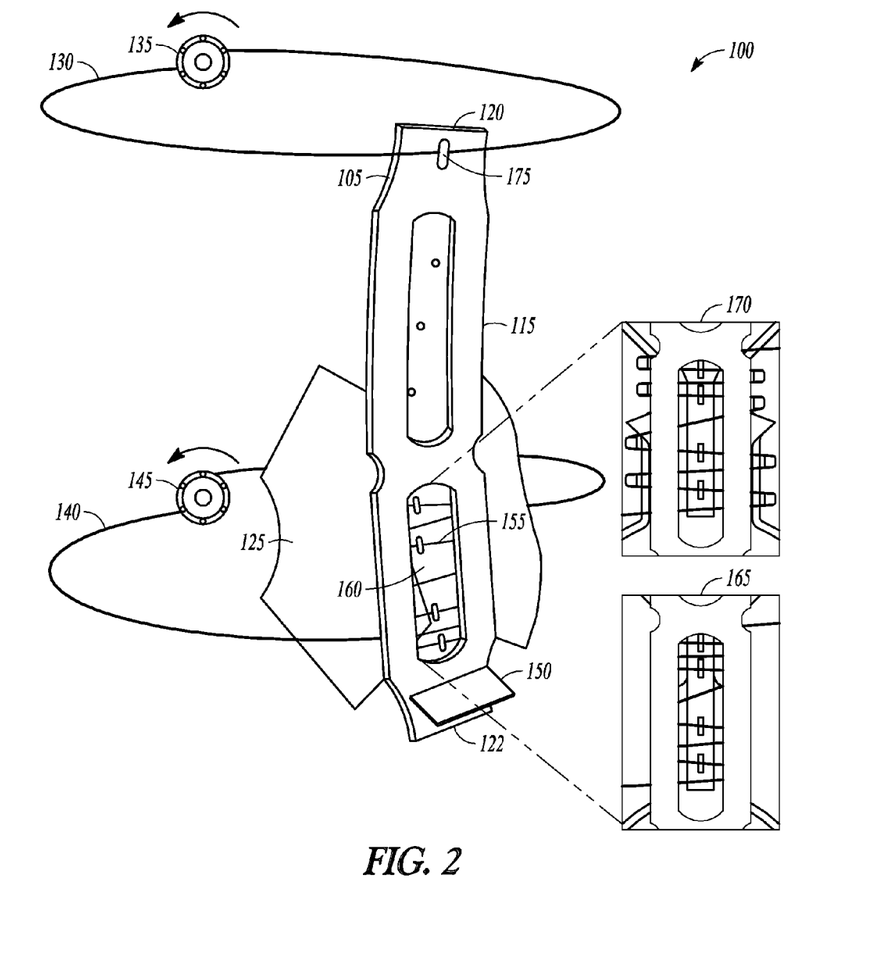
FIG. 2 is a perspective back view of an artificial spine system having an "S" shaped flexible support according to an example embodiment.

FIG. 1 is a perspective block diagram front view of a back support system 100, also referred to as an artificial spine system. The back support system 100 has an artificial spine 105 that includes a flexible support 110 for back support. FIG. 2 is a perspective block diagram of a back view of the back support system 100. In one embodiment, the flexible support 110, which may be thought of as an "S" shaped spring, is formed of a flexible, lower durometer material that has a contour "S" shape to conform to the normal shape of a human spine. In further embodiments, the "S" shape may be similar to that of a human spine while providing support at one or more points along the spine. Still other shapes with multiple layers that provide support at desired points of a spine may be used in further embodiments. In one embodiment, the flexible support 110 has a rectangular shape and a thickness selected to provide a desired spring force, ranging in average torso sizes of 12"-19" to accommodate child to adult average sizes. The length of the flexible support 110 may be selected for each wearer to run from the base of the spine to a point short of the neck. In one embodiment, the flexible support 110 extends up to between the shoulder blades of the wearer.

A stiffer, higher durometer material brace portion 115 of the artificial spine 105 is coupled to the flexible support 110 at ends 120 and 122 of a length of the flexible support 110 and operates to push the flexible support 110 into the back. The higher durometer material brace portion 115 resists bending motions of the spine, pushing the flexible support 110 harder into the back and spine of a wearer when the wearer is bending. It thus provides additional support of the spine when a wearer leans over to move or pick up a heavy object. The brace portion 115 may be completely rigid, bending very little if any, or may be less rigid in further embodiments, with a polyethylene low durometer of 54D or a high of 70D.

The artificial spine 105 is designed to be worn throughout the duration of moments of heavy lifting. It is also suggested to be worn during moments of back muscle and spine fatigue. The artificial spine 105 may be built-in or attached to garments and other soft goods as indicated at 125, which may be piece of fabric shaped to fit about a lower back portion of a wearer. When built in to a garment, the artificial spine and garment may be referred to as an artificial spine system or back support system.

The back support system 100 may be adjusted to loosen a fit when the wearer is not directly in need of support (example: sitting down) and tightened right before the time of heavy lifting by means of top wire lace 130 and coupled tension adjusting control 135, and a bottom wire lace 140 and coupled tension adjusting control 145. The adjusting controls 135 and 145 may be a wheel with an axel around which the wire winds when the wheel is turned. The wires are released as each wheel is pressed, relaxing the pressure exerted on the flexible support 110 exerted by the brace portion 115. Such controls and other suitable ratcheting controls are commercially available. In a further embodiment, a strap may be used in place of the wire with a suitable ratchet for releasable tightening the strap and drawing the brace portion 115 toward the flexible support 110.

In one embodiment, the wires may be integrated into clothing, or may include a flat laminated material positioned between the wire and a wearer to more evenly distribute force exerted by the wire on the wearer. The laminated material may be integrated into clothing in some embodiments, or may be placed over clothing, utilizing the clothing to further distribute force from the wire over a broader surface area of the wearer.

In one embodiment, as the user bends over to lift, the artificial spine automatically adjusts to the shape of the lumbar, with brace portion 115 pushing the soft flexible support portion into the back and spine of the wearer, assisting the wearer in tightening their lower back muscles.

A pant line clamp 150 is coupled proximate the bottom end 122 of the artificial spine 105 to support the flexible support in a proper position with respect to the spine of the wearer. The clamp 150 fits over a waist line of pants and/or belt, and prevents the artificial spine 105 from sliding further down the back of the wearer, keeping the flexible support 110 adjacent to the spine with a similar "S" curvature of the spine. The clamp may also prevent the flexible support from sliding upward when the wearer bends forward.

Connecting all components of the back support unit is an adjustable lacing system indicated at 155. The lacing system 155 consists of wire 140 that serpentines back and forth over a length of the garment 125, drawing together two sides of garment 125 when tightened as indicated at 165, or allowing garment 125 to widen when loosened at 170. A latch 175 may be used to guide top wire 130 and maintain it proximate end 120 when the wire is tightened or loosened. The brace portion 115 may contain one or more cut outs 160 to reduce weight and increase breathability for a wearer.

With this built in artificial spine, the wearer can safely lift and transport the weight of heavy loads. The back support system 100 provides a method for controlling the rigidness and flexibility of the flexible support 110 that can assist the user in all-day use. The ability of the back support system 100 to be both flexible and rigid facilitates adjustment to the normal body movements of the human spine in moments of walking, sitting, and lifting.

Building the back support device into a garment makes it ready and available to use. Having the device adjustable, the wearer can comfortably use it when lifting heavy loads and when sitting and walking. The flexible support creates pressure on the lower back muscles encouraging the user to lock their back to limit their range of motion and prevent hyperextension.

The back support device can be removable for replacement and for keeping the garment washable. In one embodiment, a body fluid-repellent fabric coating protects the life of the uniform from normal use. The back support system and garment can both have an athletic fit for elasticity, efficiency, and breathability. In one embodiment, the portions 110 and 115 form a combination of two plates with spine-lacing 130, 140, 155 support that provides an efficient design to create rigidity, adjustability, and flexibility for back support. In a further embodiment, an adjustable back brace/spring with a belt and shoulder straps can be worn at home over any article of clothing. Another version is a robust back brace with artificial spine/spring with padding on the straps for users who are lifting all day, with extra support around the waist.

In professional use, a heavy-duty back brace with artificial spine/spring may be built into law enforcement, fire, and EMT uniforms, among other professional needs.

An example of how the back support unit could be built into a garment is best demonstrated through an EMT uniform. The built-in adjustable back brace and flexible support for back support could be inserted into a paramedic uniform. The system in one embodiment is designed to be worn throughout the duration of a response call. It is also suggested to be worn during the time the EMT is at the station, as maintenance around the vehicle may require heavy lifting. Some EMT Paramedics average 48 hour shifts, and emergency calls can each last for several hours increasing back and muscle fatigue and jeopardizing correct posture.

The back support device can be adjusted to loosen the fit when the paramedic is not directly using the shirt/uniform (example: driving the ambulance) and tightened right before the time of heavy lifting.

As the EMT bends over to lift, the back brace automatically adjusts following the shape of the lumbar spine, assisting the EMT in tightening their lower back muscles, by adding the needed pressure to the lower back. With this built-in back brace and artificial spine (spring), EMTs can safely lift and transport patients and other heavy loads their jobs require.

Figure 3A:
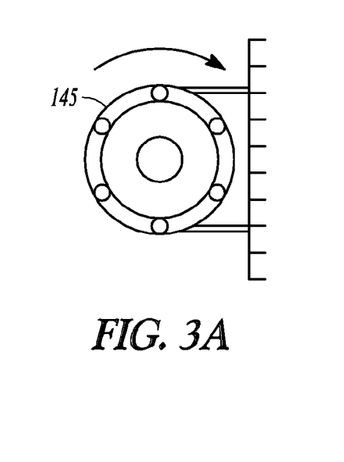
FIGS. 3A, 3B, 3C, and 3D illustrate use of a lacing system to tighten a lacing system of an artificial spine system according to an example embodiment.
Figure 3B:
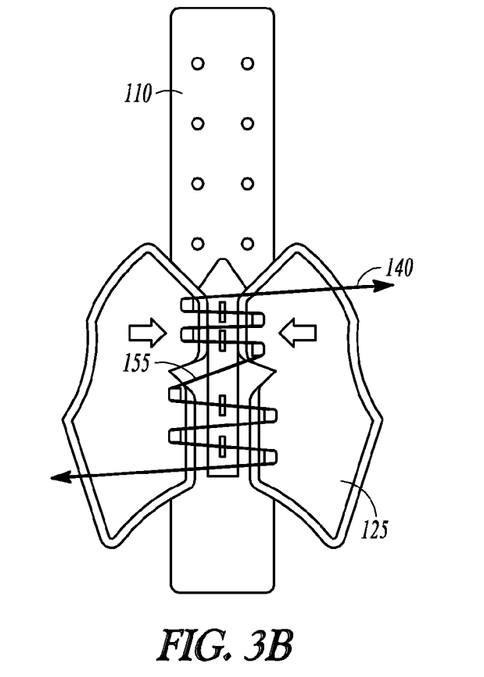
Figure 3C:
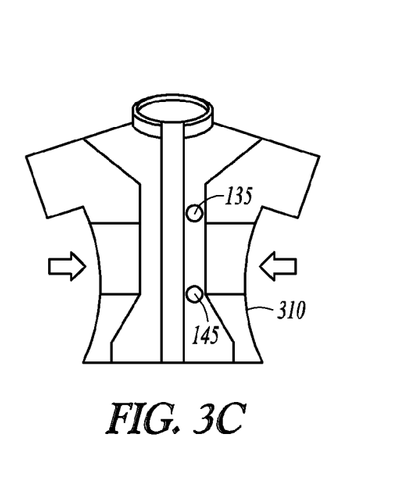
Figure 3D:
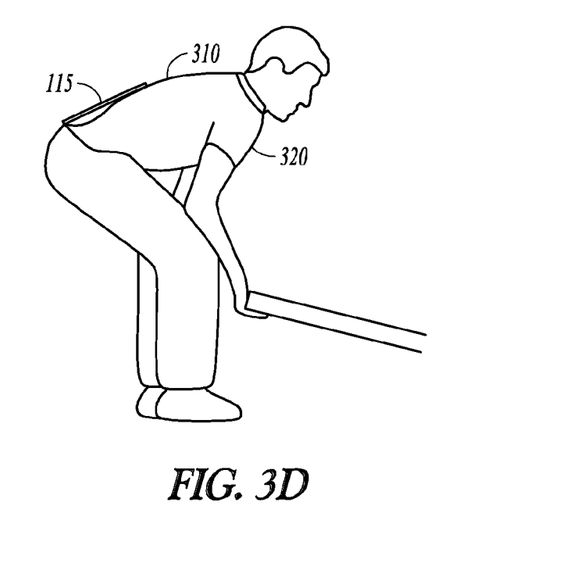

FIGS. 3A, 3B, 3C, and 3D illustrate various views of a garment 310 having an integrated back support system/artificial spine. In FIG. 3A, tension adjusting control 145 is used to tighten wire 140 and lacing 155 about the flexible support 110 as seen in FIG. 3B. A front view of the garment 310 is shown in FIG. 3C with controls 135 and 145 shown proximate the front of the garment 310 to allow a wearer to adjust the tension in the wires. The location of the controls may be positioned in various portions of the garment that allow adjustment by the wearer or other person. As seen in FIG. 3C, the garment is tighter fitting on a wearer, as the sides of the garment may also be drawn in by the tightened wires. FIG. 3D illustrates a person 320 wearing the garment 310 having an integrated artificial spine in the process of lifting. The integrated artificial spine pushes into the spine, causing the wearer not to bend the spine as much as a wearer likely would without the artificial spine.

Figure 4A:
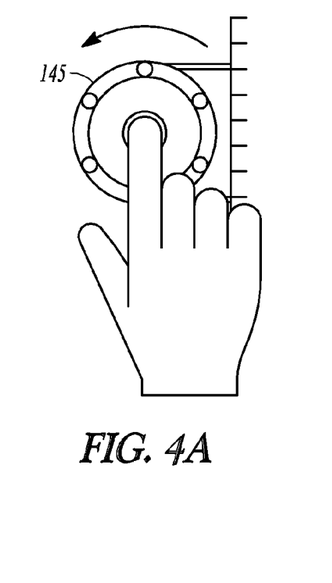
FIGS. 4A, 4B, 4C, and 4D illustrate use of a lacing system of an artificial spine system according to an example embodiment.
Figure 4B:
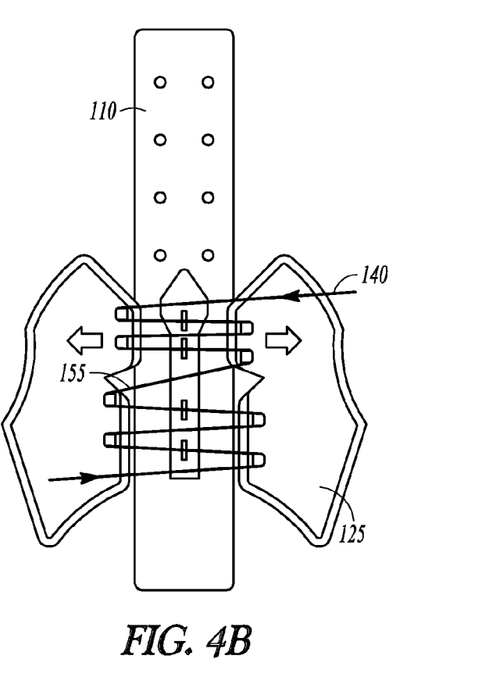
Figure 4C:
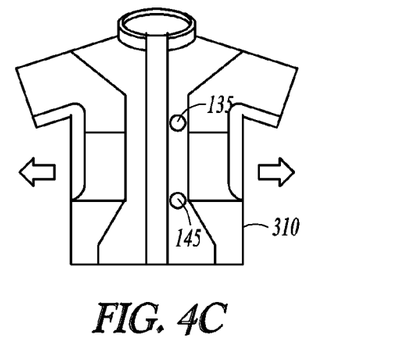
Figure 4D:
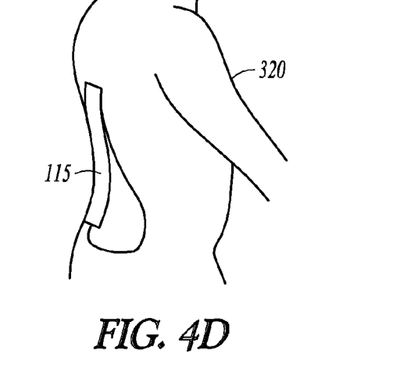

FIGS. 4A, 4B, 4C, and 4D illustrate various views of the garment 310 having an integrated back support system/artificial spine. In FIG. 4A, tension adjusting control 145 is used to loosen wire 140 and lacing 155 about the spring portion 110 as seen in FIG. 4B. A front view of the garment 310 is shown in FIG. 4C with controls 135 and 145 shown proximate the front of the garment 310 to allow a wearer to adjust the tension in the wires. As seen in FIG. 4C, the garment 310 is more loosely fitting on a wearer, as the sides of the garment are allowed to expand without being constrained by the loosened wires. FIG. 4D illustrates a person 320 wearing the garment 310 having an integrated artificial spine in the process of standing upright. The integrated artificial spine more gently pushes into the spine, causing the wearer not to maintain good posture.

Figure 5A:
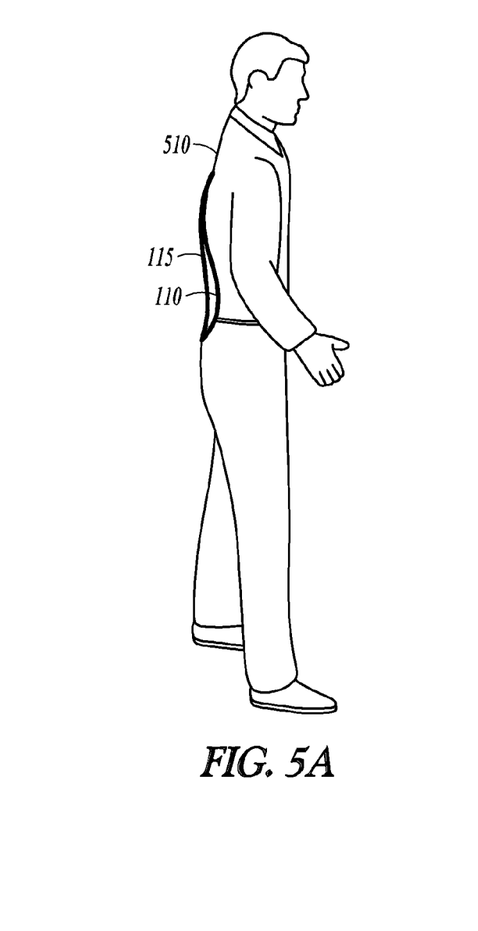
FIGS. 5A, 5B, and 5C illustrate how the "S" shaped flexible support follows the natural shape of the lumbar and the back arches over when bending down according to an example embodiment.
Figure 5B:
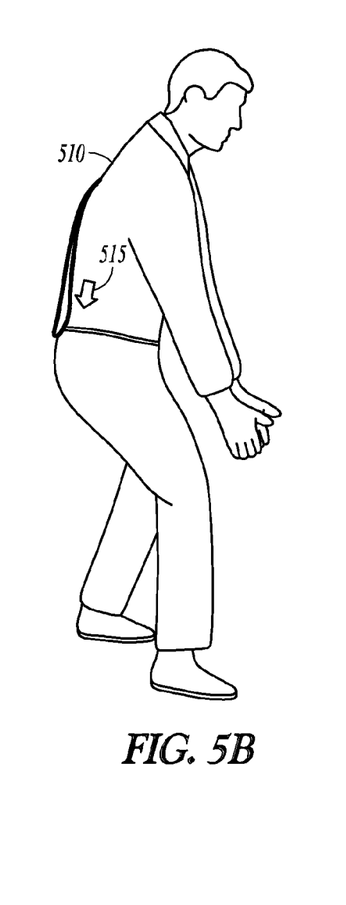
Figure 5C:
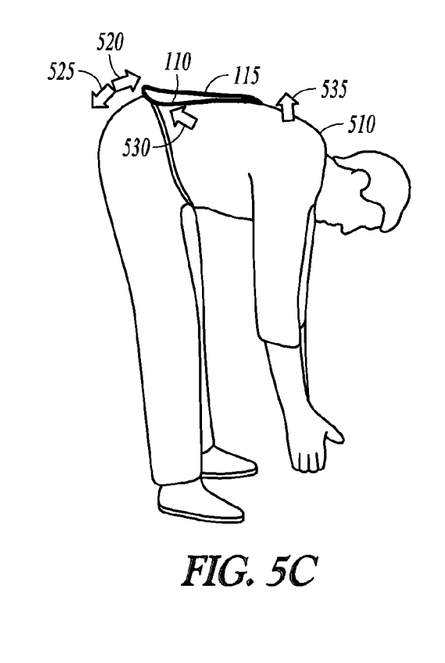

FIGS. 5A, 5B, and 5C illustrate a wearer 510 of the back support system comprising a flexible support portion 110 and brace portion 115. The wearer 510 is upright in FIG. 5A, and starts to get ready to lift in FIG. 5B, starting to bend as shown at 515 resulting in the back support adjusting to tighten the lower back of the wearer as the wearer bends forward. In FIG. 5C, the wearer is fully bent as indicated at 520 and 525, causing a hinge effect as indicated at 530, preventing hyperextension of the back of the wearer. The support of the back continues as lifting 535 occurs.

Figure 6:
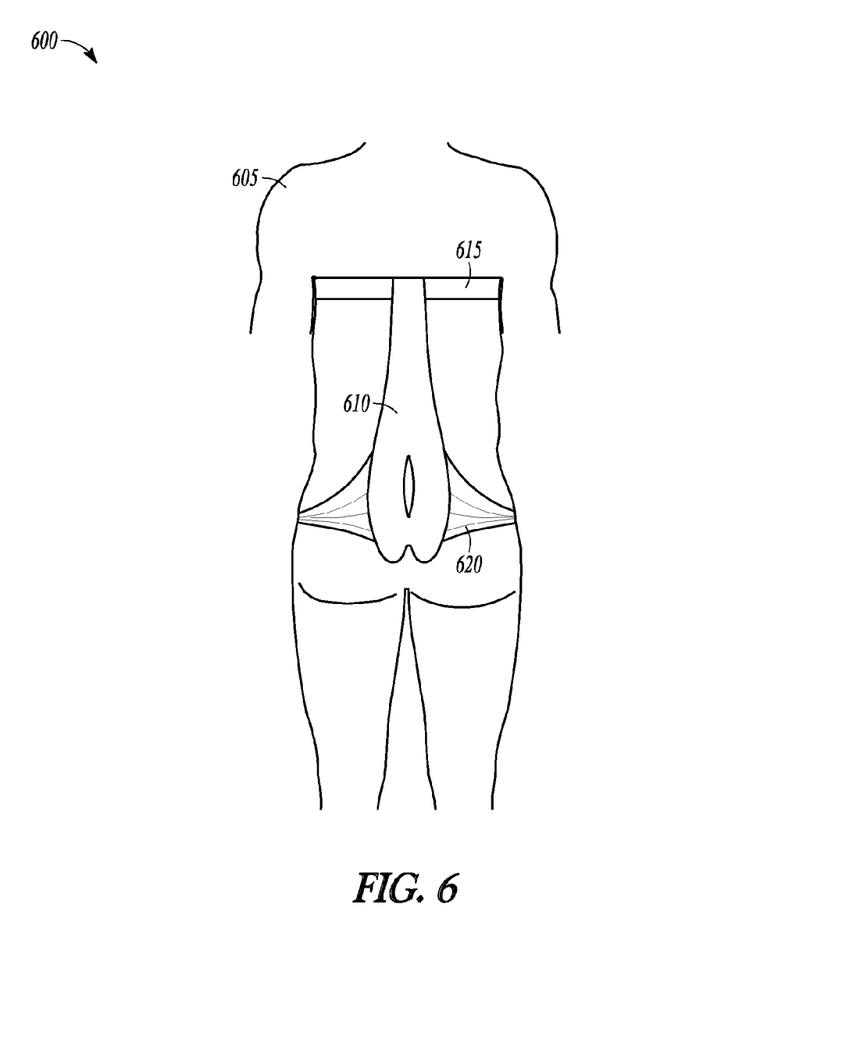
FIG. 6 is a representation of a user wearing an artificial spine system according to an example embodiment.

FIG. 6 is a representation 600 of a user 605 wearing an artificial spine 610 according to an example embodiment. Representation 600 shows one embodiment with an upper strap 615 to support the top of the artificial spine 610, and a strap 620 to support a lower part of the artificial spine 610. The lower strap may be embedded in a garment, or may be directly coupled to the brace portion of the artificial spine 610 as shown. The straps may have wires embedded in them in some embodiments, with lacing about a portion of the brace to apply pressure to the spring portion of the artificial spine when tightened. The lower strap may be positioned with respect to the brace portion above the lower end of the brace portion to provide some leverage against the spring portion of the artificial spine to support the wearer's spine. In one embodiment, the lower strap 620 is integrated at least partially into a garment about the point at which it provides adjustable force on the lower portion of the brace.

Example Materials:

The majority of a uniform may be made of bamboo fibers for abrasion resistance and durability. Other fibers providing suitable stiffness and durability may be used in further embodiments. The side panels underneath the arms may be made of Lycra or other materials. The entire uniform may optionally be sprayed with a repellant for protection against body fluids.

The artificial spine may be formed with a low density polyethylene (LDPE 54D) strip, and a high density polyethylene (HDPE 70D) strip. Reflected piping may be placed on the shoulders and side panels for light reflection.

Two plastic turn dials, with a polypropylene or metal wire, wrap around the torso and connect to the back brace portion and flexible support. Foam padding may be stitched on the inside of the back brace and flexible support for comfort.

Technical Specs and Production Method:

The pattern of the uniform may be cut out from different materials and stitched together. A top and a bottom pocket may be added along the center of the back to allow the flexible support and brace portion to slip in and out. The pattern may follow average male, female, and children sizes. The back brace and flexible support may be cut from polyethylene strips. The strips are then bent to the natural "S" shape of the lumbar and secured together using round rivets or other suitable fasteners, such as adhesives, clamps, etc. The side garments are cut to their exact shape and laced together using the wire. The back brace and flexible support forming the artificial spine may be inserted into pockets along the center of the back, and the wire is run through the inside of the uniform to connect to the turn dials in the front.

EXAMPLES

1. A back support device comprising:
    a flexible support adapted to be positioned adjacent a spine of a wearer, the flexible support extending along the spine in an "S" shape; and
    a brace portion coupled to the flexible support at ends of the flexible support, adapted to force the flexible support portion toward the spine as a wearer bends.

2. The back support device of example 1 and further comprising an adjustable tension wire positioned to extend around a wearer and tighten the brace portion against the flexible support portion.

3. The back support device of any of examples 1-2 wherein the adjustable tension wire further includes a tension adjusting control coupled to the wire to releasable tighten the tension wire.

4. The back support device of any of examples 1-3 wherein the adjustable tension wire is coupled to a laminated shield to reside between the wire and a body of a wearer to spread force from the wire over a portion of the body wider than the width of the wire.

5. The back support device of any of examples 1-4 wherein the brace portion contains an opening, and wherein the adjustable tension wire forms a serpentine path about the garment portion.

6. The back support device of any of examples 1-5 wherein the adjustable tension wire is coupled to the brace portion about a portion of the brace portion proximate a lower back portion of a wearer.

7. The back support device of any of examples 1-6 and further comprising an upper adjustable tension wire coupled to the brace portion about an upper portion of the brace portion.

8. The back support device of any of examples 1-7 and further comprising a garment portion disposed between the flexible support portion and the brace portion.

9. The back support device of any of examples 1-8 and further comprising a clamp positioned about a lower end of the brace portion, the clamp adapted to support the back support proximate a wearer's spine by supporting the back support by clothing worn about the waist of the wearer.

10. The back support device of any of examples 1-9 and further comprising a garment having the brace portion and flexible support portion integrated into the garment, and having an upper and a lower lacing integrated into the garment.

11. The back support device of example 10 and further comprising a pair of respective tightening controls coupled to respective upper and lower lacing and supported by the garment in a position accessible to the wearer to control force on the wearer's spine generated by the brace portion pushing the flexible support portion toward the spine.

12. A method comprising:
    placing a flexible support adjacent a spine of a wearer, the flexible support extending along the spine in an "S" shape; and
    coupling a brace portion to the flexible support at ends of the flexible support, wherein the brace portion is positioned to force the flexible support portion toward the spine as a wearer bends.

13. The method of example 12 and further comprising using an adjustable tension wire positioned to extend around a wearer to tighten the brace portion against the flexible support portion.

14. The method of example 13 wherein tightening is performed using a tension adjusting control coupled to the wire to releasable tighten the tension wire.

15. The method of example 14 wherein the adjustable tension wire is coupled to a laminated shield to reside between the wire and a body of a wearer to spread force from the wire over a portion of the body wider than the width of the wire.

16. The method of example 13 wherein the adjustable tension wire is coupled to the brace portion about a portion of the brace portion proximate a lower back portion of a wearer.

17. The method of example 13 wherein tightening further utilizes an upper adjustable tension wire coupled to the brace portion about an upper portion of the brace portion.

18. The method of any of examples 12-17 and further comprising integrating the flexible support portion and the brace portion into a garment.

19. The method of any of examples 12-18 and further comprising providing a clamp positioned about a lower end of the brace portion, the clamp adapted to support the back support proximate a wearer's spine by supporting the back support by clothing worn about the waist of the wearer.

20. The method of example 12 and further comprising integrating the brace portion and flexible support portion into the garment, and integrating an upper and a lower lacing into the garment with a pair of respective tightening controls coupled to respective upper and lower lacing and supported by the garment in a position accessible to the wearer to control force on the wearer's spine generated by the brace portion pushing the flexible support portion toward the spine.

21. A method for controlling the rigidness and flexibility of an artificial spine device that can assist the user in all-day use. This would have the ability of the back support device to be both flexible and rigid and adjust to the normal body movements of the human spine in moments of walking, sitting, and lifting.

22. A method for controlling the rigidness and flexibility of an artificial spine that can assist the user in all-day use. The artificial spine would be placed vertically along the center of the human spine. The flexible support would bent and shaped to the natural "S" shape of the human lumbar spine. This method would allow the artificial spine to always be pressed against the human spine adding support. Since the material of the flexible support is flexible, it would follow the movement and shape of the lumbar spine.

23. A method of bringing together a garment of overlapping sliding soft material plates using a lacing system to create support for the lower back muscles. The material plates can come together and separate by adjusting the lacing system.

24. A method of attaching the lower part of the flexible support to the top section of the brace portion. This method would create a "hinge" at the fulcrum point of the waist that could control the movement of the user when bending forward to prevent hyperextension. This method would also add needed support and pressure to the lower back muscles as the flexible support follows the "bow" shape of the lumbar spine when bending forward.

25. A method of creating a lacing system that weaves together a garment of soft material plates coupled to the brace portion, and wraps around the torso to connect to the front control dials. This method would allow for a secure adjustable fit of the brace portion and flexible support to be pressed against the human back.

26. The method according to any of examples 21-25 would allow for the back support device (back brace plus artificial spine (spring)) to be inserted or removed from apparel and other types of garments and soft goods.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A back support device comprising:
   an "S" shaped flexible spring support adapted to be positioned adjacent a spine of a wearer, the flexible spring support extending along the spine of the wearer when worn; and
   a brace plate including two ends directly portion coupled to the flexible spring support at ends of the flexible spring support, wherein the brace plate defines a portion that extends directly between one coupled end to the other coupled end, and wherein the portion is positioned behind and spaced from the flexible spring support.

2. The back support device of claim 1 and further comprising an adjustable tension wire positioned to extend around a wearer and when tightened, to draw the brace plate toward— the flexible spring support.

3. The back support device of claim 2, wherein the adjustable tension wire further includes a tension adjusting control coupled to the wire to releasable tighten the tension wire.

4. The back support device of claim 3, wherein the adjustable tension wire is coupled to a laminated shield adapted to reside between the wire and a body of a wearer to spread force from the wire over a portion of the body wider than the width of the wire.

5. The back support device of claim 2, wherein the brace plate contains an opening, and wherein the adjustable tension wire forms a serpentine path about a garment.

6. The back support device of claim 2, wherein the adjustable tension wire is coupled to the brace plate about a portion of the brace portion proximate a lower back portion of a wearer.

7. The back support device of claim 2 and further comprising an upper adjustable tension wire coupled to the brace plate about an upper portion of the brace plate.

8. The back support device of claim 1, wherein the brace plate is formed of a higher durometer material than the flexible spring support to resist bending motion of the spine and push the flexible spring support harder into a back of the wearer when the wearer bends.

9. The back support device of claim 1 and further comprising a clamp positioned about a lower end of the brace plate, the clamp adapted to support the back support device proximate a wearer's spine by supporting the back support by clothing worn about a waist of the wearer.

10. The back support device of claim 1 and further comprising a garment having the brace plate and flexible spring support integrated into the garment, and having an upper and a lower lacing integrated into the garment.

11. The back support device of claim 10 and further comprising a pair of respective tightening controls coupled to respective upper and lower lacing and supported by the garment in a position accessible to the wearer to control force on the wearer's spine generated by the brace plate pushing the flexible spring support toward the spine.

12. A method of wearing a back support device, the method comprising:
   placing an "S" shaped flexible spring support adjacent a spine of a wearer, the flexible spring support extending along the spine of the wearer when worn; and
   coupling a brace plate including two ends directly to the flexible spring support at ends of the flexible spring support, wherein the brace plate defines a portion that extends directly between one coupled end to the other coupled end, and wherein the portion is positioned behind and is spaced from the flexible spring support.

13. The method of claim 12 and further comprising using an adjustable tension wire positioned to extend around a wearer to tighten the portion against the flexible spring support.

14. The method of claim 13 wherein tightening is performed using a tension adjusting control coupled to the adjustable tension wire to release and tighten the adjustable tension wire.

15. The method of claim 14 wherein the adjustable tension wire is coupled to a laminated shield adapted to reside between the wire and a body of a wearer to spread force from the wire over a portion of the body wider than the width of the wire.

16. The method of claim 13 wherein the adjustable tension wire is coupled to the brace plate about a portion of the brace portion proximate a lower back portion of the wearer.

17. The method of claim 13 wherein tightening further utilizes an upper adjustable tension wire coupled to the brace plate about an upper portion of the brace portion.

18. The method of claim 12 and further comprising integrating the flexible spring support and the brace plate into a garment.

19. The method of claim 12 and further comprising providing a clamp positioned about a lower end of the brace plate, the clamp adapted to support the back support proximate the wearer's spine by supporting the back support by clothing worn about a waist of the wearer.

20. The method of claim 12 and further comprising integrating the brace plate and flexible spring support into a garment, and integrating an upper and a lower lacing into the garment with a pair of respective tightening controls coupled to respective upper and lower lacing and supported by the garment in a position accessible to the wearer to control force on the wearer's spine generated by the brace plate pushing the flexible spring support toward the spine.

\* \* \* \* \*